(12) United States Patent
Deason et al.

(10) Patent No.: US 6,401,540 B1
(45) Date of Patent: Jun. 11, 2002

(54) METHOD AND APPARATUS FOR DETECTING INTERNAL STRUCTURES OF BULK OBJECTS USING ACOUSTIC IMAGING

(75) Inventors: Vance A. Deason; Kenneth L. Telschow, both of Idaho Falls, ID (US)

(73) Assignee: Bechtel BWXT Idaho, LLC, Idaho Falls, ID (US)

(*) Notice: Subject to any disclaimer, the term of this patent is extended or adjusted under 35 U.S.C. 154(b) by 0 days.

(21) Appl. No.: 09/515,823

(22) Filed: Feb. 29, 2000

(51) Int. Cl.[7] .......................... G01B 9/02; G01N 29/06
(52) U.S. Cl. ........................ 73/657; 356/357
(58) Field of Search ................ 73/656, 657, 655; 356/357, 349, 358, 354, 350, 360, 347, 345, 432

(56) References Cited

U.S. PATENT DOCUMENTS

| | | | | |
|---|---|---|---|---|
| 3,670,098 A | * | 6/1972 | Korpel | 178/6 |
| 3,772,457 A | * | 11/1973 | Macovski | 178/6.8 |
| 4,070,643 A | | 1/1978 | Green | 340/5 |
| 4,284,324 A | * | 8/1981 | Huignard et al. | 350/3.64 |
| 4,561,410 A | | 12/1985 | Crostack | 73/603 |
| 4,561,411 A | | 12/1985 | Collins et al. | 73/603 |
| 4,631,965 A | | 12/1986 | De Vadder et al. | 73/602 |
| 4,905,202 A | | 2/1990 | Robillard | 367/8 |
| 5,131,748 A | * | 7/1992 | Monchalin et al. | 356/349 |
| 5,402,235 A | * | 3/1995 | Monechalin | 356/357 |
| 5,827,971 A | * | 10/1998 | Hale et al. | 73/657 |
| 6,134,006 A | * | 10/2000 | Telschow et al. | 356/357 |
| 6,175,411 B1 | * | 1/2001 | Telschow et al. | 356/357 |

OTHER PUBLICATIONS

Leeman, S., et al, "Field Propagation via the Angular Spectrum Method," *Accoustical Imaging*, vol. 23, 1997 pp. 363–368.

Wirgin, A., et al, "Shape Reconstruction of a Penetrable Scattering Body via Diffracted Waves and Canonical Solutions," *Accoustical Imaging*, vol. 23, 1997 pp. 459–464.

Telschow, K.L., et al, "INEEL Laser Ultrasonic Measurements on Paper," published Jan. 1999.

Telschow, K.L., et al, "Material Property Measurement of Metallic Parts Using the INEEL Laser Ultrasonic Cameral," published Aug. 1999.

Brenden, B.B., "Acoustical Holograpy," *Optical and Acoustical Holograpy*, Plenum Press, 1972 pp. 347–402.

Tabei, M., et al, "Holographic Reconstruction of Acoustic Fileds by Discrete Convolution," *Acoustical Imagining*, vol. 23, 1997, pp. 453–458.

* cited by examiner

Primary Examiner—Hezron Williams
Assistant Examiner—Rose M. Miller
(74) *Attorney, Agent, or Firm*—Dahl & Osterloth, LLP

(57) ABSTRACT

Apparatus for producing an acoustic image of an object according to the present invention may comprise an excitation source for vibrating the object to produce at least one acoustic wave therein. The acoustic wave results in the formation of at least one surface displacement on the surface of the object. A light source produces an optical object wavefront and an optical reference wavefront and directs the optical object wavefront toward the surface of the object to produce a modulated optical object wavefront. A modulator operatively associated with the optical reference wavefront modulates the optical reference wavefront in synchronization with the acoustic wave to produce a modulated optical reference wavefront. A sensing medium positioned to receive the modulated optical object wavefront and the modulated optical reference wavefront combines the modulated optical object and reference wavefronts to produce an image related to the surface displacement on the surface of the object. A detector detects the image related to the surface displacement produced by the sensing medium. A processing system operatively associated with the detector constructs an acoustic image of interior features of the object based on the phase and amplitude of the surface displacement on the surface of the object.

16 Claims, 5 Drawing Sheets

METHOD AND APPARATUS FOR DETECTING INTERNAL STRUCTURES OF BULK OBJECTS USING ACOUSTIC IMAGING

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

FIELD OF THE INVENTION

This invention relates to acoustic imaging in general and more specifically to a method and apparatus for detecting internal structures in bulk objects using acoustic imaging.

BACKGROUND OF THE INVENTION

Various types of acoustic imaging processes have been developed over the years in which an acoustic wave is used to collect information relating to certain internal features and structures in objects. Acoustic imaging processes are useful for this purpose since acoustic waves pass easily through most objects.

While some types of acoustic imaging processes utilize only the amplitude of the acoustic wave in order to detect certain internal features and structures of the object, it is known that considerably more information may be obtained about such internal features if both the phase and the amplitude of the acoustic wave are captured. Consequently, many acoustic imaging processes have been developed which capture both the phase and amplitude of the acoustic wave after it has traveled through the object. Once the phase and amplitude have been captured, any of a wide variety of processing methods and/or wave reconstruction techniques may be used to produce an "acoustic" image of the object. Depending on the particular processing method that is used, the resulting acoustic image may reveal certain interior features, structures, and/or faults which may be contained within the object.

While systems for producing such acoustic images are known and have been used, such systems are not without their problems. For example, one significant problem that heretofore has imposed significant limitations on acoustic imaging processes relates to capturing the phase and amplitude of the acoustic wave. Any errors or distortions that may arise from or be introduced in the acoustic wave capturing process will adversely affect the resulting acoustic image data unless suitable processes or methods are employed to compensate for any such errors or distortions.

For example, in one type of acoustic imaging system, a two-dimensional array of microphones is used to capture and record both the phase and amplitude of the acoustic wave emanating from the ensonified object. Unfortunately, however, the physical size of each microphone prevents a two-dimensional array of such microphones from collecting little more than a relatively coarse, sampling of the phase and amplitude of the acoustic wave. Such coarse sampling limits the spatial resolution available with such a process. Another problem with such microphone systems is that the microphones are typically located a spaced-distance from the surface of the ensonified object. The intermediate medium (e.g., air) located between the object surface and the microphones distorts the acoustic data which, if not fully and correctly removed or compensated, distorts the final acoustic image data. The removal or compensation of such distortions is by no means trivial, and to date, no system has been developed that fully and completely compensates for the distortion arising from the passage of the acoustic wave through the intermediate medium (e.g., air). Moreover, the presence of air between the surface of the ensonified object and the microphones also tends to limit the sensitivity of the acoustic imaging system.

Partly in an effort to solve the spatial resolution problem associated with the use of a two-dimensional array of microphones, acoustic imaging processes have been developed in which the two-dimensional array of microphones is replaced by a single microphone. This single microphone is then scanned in two-dimensions in a raster-like manner in order to record the phase and amplitude of the acoustic wave emanating from the ensonified object. While the single microphone scanning system allows for increased spatial resolution, it is limited in temporal resolution in that it requires a finite time to move the scanning microphone over the desired data collection area. Consequently, such scanning type systems are only useful if the acoustic wave pattern is essentially time invariant during the period required to complete the scan. That is, if the acoustic wave pattern changes during the scan, the resulting acoustic image data will be distorted. Of course, such single microphone systems are still prone to the distortion problems resulting from the fact that the acoustic waves travel through the intermediate medium (e.g, air) before reaching the microphone.

Another class of acoustic imaging systems, generally referred to as immersion type systems, require that the object to be studied be immersed in a liquid, such as water. The liquid acts as an acoustical amplifier, thereby increasing the sensitivity of the acoustic imaging system over systems in which air comprises the intermediate medium. In one type of immersion process, a suitable object acoustic wave generator is placed in the liquid along with the object and is used to ensonify the object. This results in the production of an object wave which eventually reaches the surface of the liquid. The object wave is then combined with a reference acoustic wave which is produced by a separate reference wave generator that is also submerged within the liquid. The reference and object waves combine and interfere with one another, resulting interference pattern on the surface of the liquid. The interference pattern forms a diffraction grating that is capable of diffracting light. The surface of the liquid is then illuminated by a coherent light source, such as a laser beam, which is thereafter diffracted by the acoustic wave interference pattern on the liquid surface. The diffracted light beam is then combined with a reference light beam to form an optical hologram that is related to the acoustic wave contained on the surface of the object. The information contained in the optical hologram of the liquid surface may be used to extract the phase and amplitude information of the acoustic wave.

One advantage of the immersion system described above is that:it does not experience the same spatial or temporal resolution problems that are typically associated with the microphone systems described above, since the optical hologram of the liquid surface may be resolved to very high resolutions. Unfortunately, however, such immersion systems are still prone to the difficulties associated with the intermediate medium (e.g., the liquid) located between the ensonified object and the "detector" (e.g., the surface of the liquid). Here again, while methods have been developed which can partially compensate for the distortions produced by the intermediate medium, the correction methods are not complete and still result in acoustic image data having a considerable degree of distortion. Of course, another disadvantage associated with such liquid immersion methods is the requirement that the object be submerged in the liquid medium.

Consequently, a need remains for an acoustic imaging system that is capable of recording both the phase and amplitude information of the acoustic wave, but is not subject to the problems and limitations associated with prior art systems. Additional advantages could be realized if such an acoustic imaging system eliminated the need for is an intermediate medium (e.g., air or a liquid) in order to carry or transmit the acoustic wave from the ensonified object to the detector system.

SUMMARY OF THE INVENTION

Apparatus for producing an acoustic image of an object according to the present invention may comprise an excitation source for vibrating the object to produce at least one acoustic wave therein. The acoustic wave produced in the object results in the formation of at least one surface displacement on the surface of the object. A light source produces an optical object wavefront and an optical reference wavefront and directs the optical object wavefront toward the surface of the object. The interaction of the optical object wavefront with the surface displacement on the object produces a modulated optical object wavefront. A modulator operatively associated with the optical reference wavefront modulates the optical reference wavefront in synchronization with the acoustic wave to produce a modulated optical reference wavefront. A sensing medium positioned to receive the modulated optical object wavefront and the modulated optical reference wavefront combines the modulated optical object and reference wavefronts to produce an image related to the surface displacement on the surface of the object. A detector detects the image related to the surface displacement produced by the sensing medium. A processing system operatively associated with the detector constructs an acoustic image of interior features of the object based on the phase and amplitude of the surface displacement on the surface of the object.

Also disclosed is a method for detecting an internal structure of an object that is comprises the steps of: Vibrating the object to produce at least one acoustic wave therein; directing an optical object wavefront toward the surface of the object so that the optical object wavefront is modulated by the surface displacement on the object to produce a modulated optical object wavefront; modulating an optical reference wavefront in synchronization with the vibrating object to produce a modulated optical reference wavefront so that a difference frequency between the modulated optical object wavefront and the modulated optical reference wavefront is within the response range of a sensing medium; combining the modulated optical object wavefront and the modulated optical reference wavefront within the sensing medium to produce an image of the surface displacement on the object; and detecting the internal feature of the object based on the image of the surface displacement.

BRIEF DESCRIPTION OF THE DRAWING

Illustrative and presently preferred embodiments of the invention are shown in the accompanying drawing in which.

DETAILED DESCRIPTION OF THE INVENTION

Figure 1:
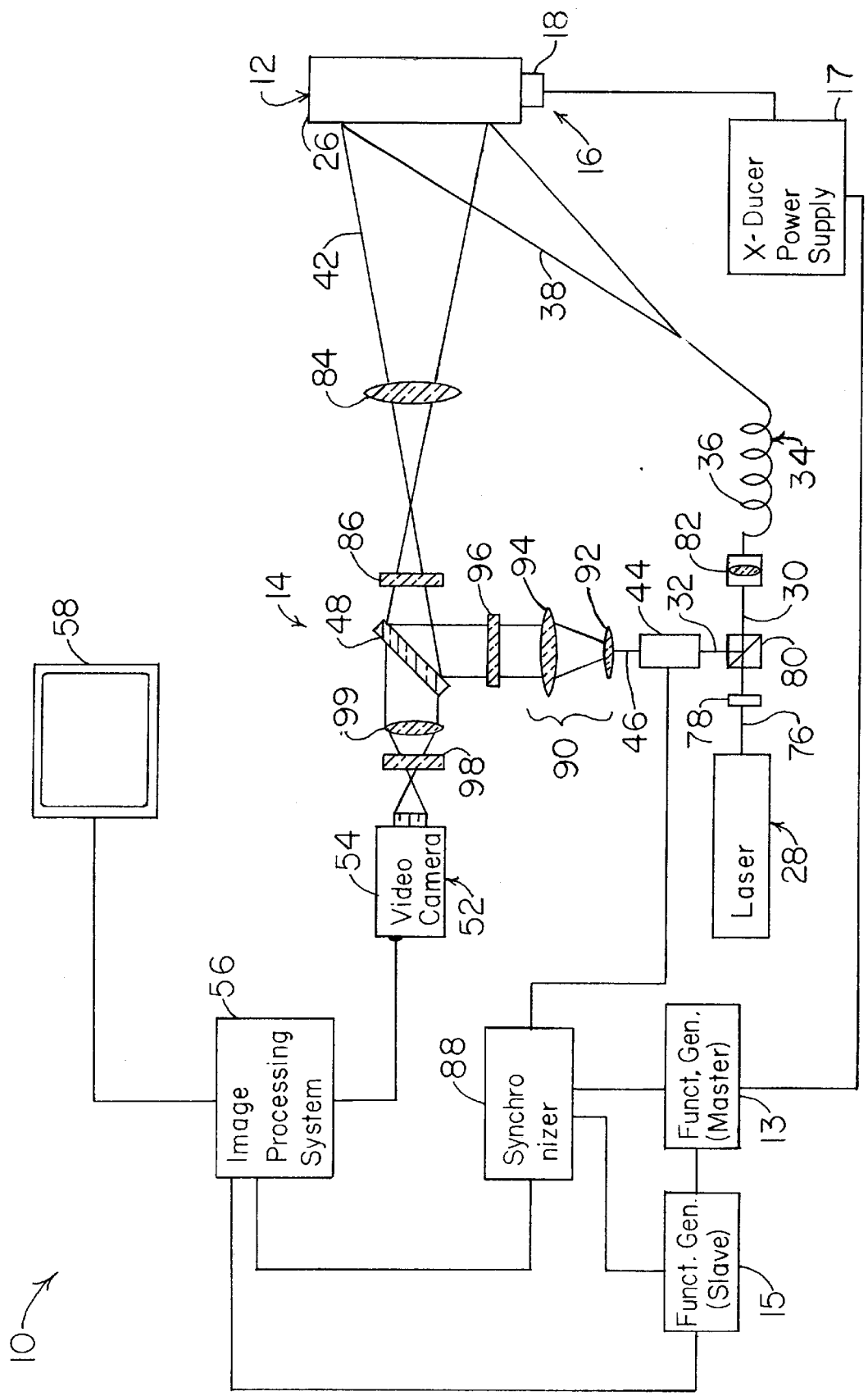
FIG. 1 is a schematic representation of an acoustic imaging apparatus according to one embodiment of the present invention.

One embodiment of an acoustic imaging apparatus 10 according to the present invention is shown in FIG. 1 as it may be used to capture and record the surface displacements produced on the surface 26 of an object 12 by an excitation source 16. For example, in the embodiment shown aid described herein, the acoustic imaging apparatus 10 captures and records the phase and amplitude of at least one surface displacement 24 (FIGS. 2a and 2b) contained on the surface 26 of the object 12. Thereafter, the phase and amplitude information may be processed by an image processing system 56 to produce an acoustic image (not shown) that is indicative of certain interior features, structures, and/or faults that may be contained in an object 12. As will be described in greater detail below, any of a wide range of acoustic image processing methods that are now known in the art or that may be developed in the future may be used to process the phase and amplitude data to generate the final acoustic image.

Figure 2A:
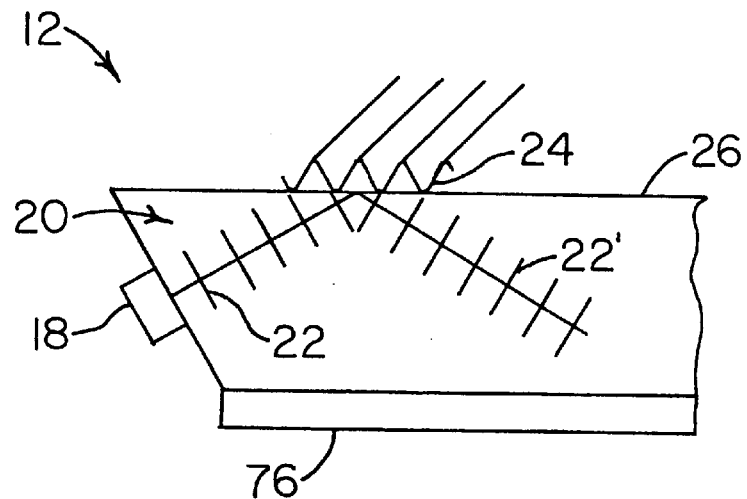
FIG. 2(a) is a diagrammatic representation of the surface displacements which may be produced in a first portion of an object by the excitation source.

With reference now primarily to FIGS. 1 and 2a, the acoustic imaging apparatus 10 that may be used to collect phase and amplitude data of a surface displacement 24 for later processing may comprise an excitation source 16, such as an acoustic transducer 18, for producing one or more acoustic waves 20 (FIG. 2a) in the object 12. The acoustic waves 20 may comprise elastic or compressive waves 22 which typically result in the formation of at least one surface displacement 24. The elastic or compressive waves 22 generally exist within the object 12, whereas the surface displacements 24 are formed on the surface 26 of object 12 by the interaction of the elastic or compressive waves 22 with the surface 26 of object 12. See FIG. 2a. That is, when an elastic or compressive wave 22 traveling within the object 12 is incident on surface 26 of object 12, some of the energy contained in the incident elastic or compressive wave 22 will be reflected by the surface 26 as a reflected elastic or compressive wave 22'. However, the reflection process will also typically result in the formation of one or more surface displacements 24 on the surface 26 of object 12.

Figure 2B:
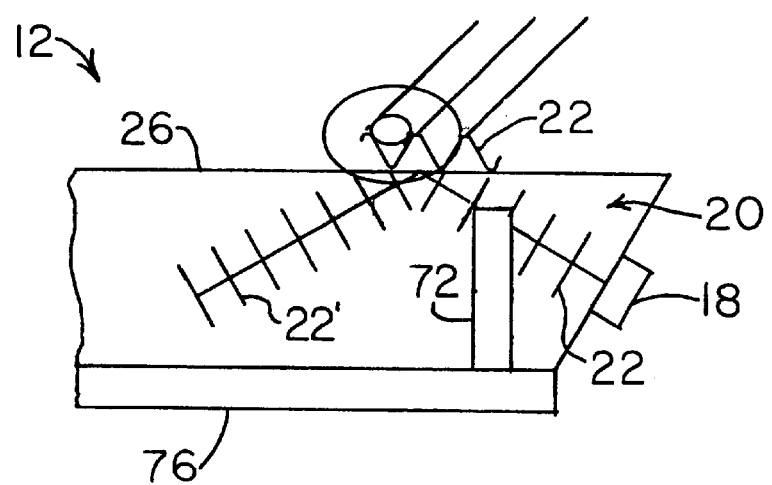
FIG. 2(b) is a diagrammatic representation of the: surface displacements which may be produced in a second portion of the object having a flat bottomed hole contained therein.
Figure 4:
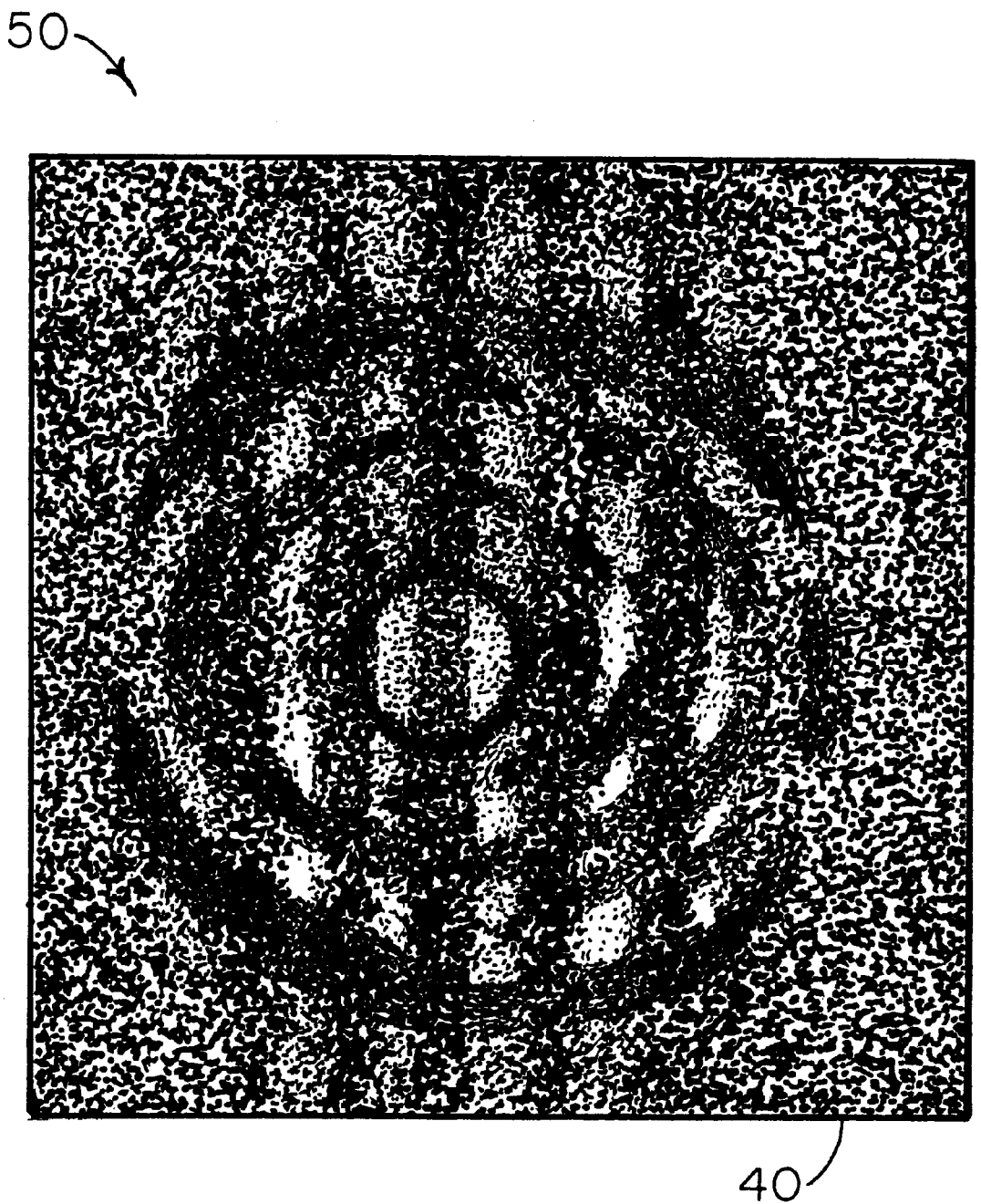
FIG. 4 is a diagrammatic representation of an image of surface displacements on a second portion of the object illustrated in FIG. 2(b) reconstructed from an optical hologram produced by the photorefractive imaging system.

The surface displacements 24 produced on the surface 26 of the object 12 carry information or data (generally in the form of phase and amplitude variations, although other forms of surface displacements can and may be detected by the present invention) that are representative of certain interior features, structures, and/or faults contained in the object 12. For example, if the object 12 is provided with a flat-bottomed hole 72 therein, as shown in FIG. 2b, the elastic or compressive waves 22 and surface displacements 24 encountering the hole 72 will be reflected, diffracted, and otherwise disturbed by the hole 72, resulting in a surface displacement pattern having phase and amplitude variations substantially as illustrated in FIG. 4. In the present invention, the phase and amplitude variations contained in this surface displacement pattern are captured and recorded by a photorefractive imaging system 14. Thereafter, the phase and amplitude data are used by the image processing system 56 to produce an acoustic image (not shown) of the object. 12 that shows features of the hole 72.

The photorefractive imaging system 14 that is used to detect the phases and amplitudes of the surface displacements 24 is best seen in FIG. 1. As used herein, the term "photorefractive" refers to a process wherein an index of refraction optical grating is produced within a sensing medium with either in-phase, out-of-phase, or of some combination of phase with respect to the intensity distribution due to the optical beams. In the embodiment shown and described herein, the photorefractive imaging system 14 may comprise a light source assembly 28 which produces two mutually coherent optical (e.g., light) beams or wavefronts: An optical object beam or wavefront 30 and an optical reference beam or wavefront 32. An optical beam confining and directing device 34, such as a fiber optic cable 36, operatively associated with the optical object beam 30 spreads and directs the optical object beam 30 onto the surface 26 of the object 12 as an expanded optical object beam 38. The expanded optical object beam 38 illuminates a two-dimensional area or region 40 (shown in FIGS. 3 and 4) on the surface 26 of object 12. Thereafter, the surface displacement (or displacements) 24 on the vibrating object 12 modulates the phase of the expanded optical object wavefront or beam 38 to form a phase modulated optical object wavefront or beam 42.

The optical reference beam or wavefront 32 produced by the light source assembly 28 is directed through a beam modulator 44 which produces a modulated is optical reference beam 46. As will be explained in greater detail below, the beam modulator 44 modulates the phase of the optical reference beam 32 at a frequency that is slightly different than the frequency of the surface displacement 24 sought to be detected on the surface 26 of object 12. The modulated optical reference beam or wavefront 46 is then directed toward a sensing medium 48 wherein the modulated optical reference beam 46 is combined with the modulated optical object beam 42 reflected by the vibrating surface 26 of object 12.

In the embodiment shown and described herein, the sensing medium 48 may comprise a photorefractive material, such as a bismuth silicon oxide crystal. When the modulated optical object and reference beams 42 and 46 are recombined within the photorefractive sensing medium 48, they create a space charge field (not shown) having a magnitude that is directly proportional to the vibrational displacement (i.e., amplitude) of the surface displacement 24 on the surface 26 of object 12 and that is a cosine function of the vibration phase of the surface displacement 24, for surface displacements 24 having small amplitudes. The space charge field modulates the local refractive index of the sensing medium 48 via the electro-optical effect, creating a diffraction grating within the sensing medium 48 that embodies the desired low-frequency phase information. The result is the formation of a hologram (not shown) which may be used to reconstruct an image 50 (illustrated generally in FIGS. 3 and 4) of the surface displacement 24 on the surface 26 of vibrating object 12. The intensity variations of the reconstructed image 50 are proportional to the phase difference between the modulated object and reference beams 42 and 46, respectively, thus surface displacement 24.

The image 50 (e.g., the image 50 illustrated in FIGS. 3 and 4) reconstructed from the hologram (not shown) produced within the photorefractive sensing medium 48 may be detected by suitable two-dimensional detector 52, such as a video camera 54. That is, the image 50 is a "real time" image which may be detected and captured at video frame rates. As will be explained in greater detail below, it is generally preferred, but not required, to further process the data contained in the image 50 in order to produce an "acoustic image" that may more directly indicate certain internal features, structures, and/or faults which may be contained within the object 12. However, such additional processing may not be required depending on the type of structures that are desired to be imaged. For example, in certain embodiments of the invention it is possible that the image 50 may, by itself and without additional processing, reveal sufficient information about certain desired internal features of the object 12. Accordingly, the present invention should not be regarded as being limited to use with the additional image processing steps performed by the image processing system 56.

Assuming, however, that it is necessary or at least desirable, to further process the data contained in the image: 50 to more directly indicate certain internal features, structures, and/or faults which may be contained in the object 12, the apparatus of the present invention may be provided with an image processing system 56. In the embodiment shown and described herein, the image processing system 56 is connected to detector 52 (e.g., video camera 54) and is used to process the real time image data (not shown) produced by the detector 52 according to any of a variety of acoustic image processing methods that are now known in the art or that may be developed in the future. After the image data have been processed, the image processing system 56 may then present an "acoustic" image (not shown) on a suitable display device 58. Depending on the particular acoustic imaging process that is utilized by the image processing system 56, the acoustic image may reveal information regarding certain interior features, structures, and/or faults contained within the object 12.

Figure 5:
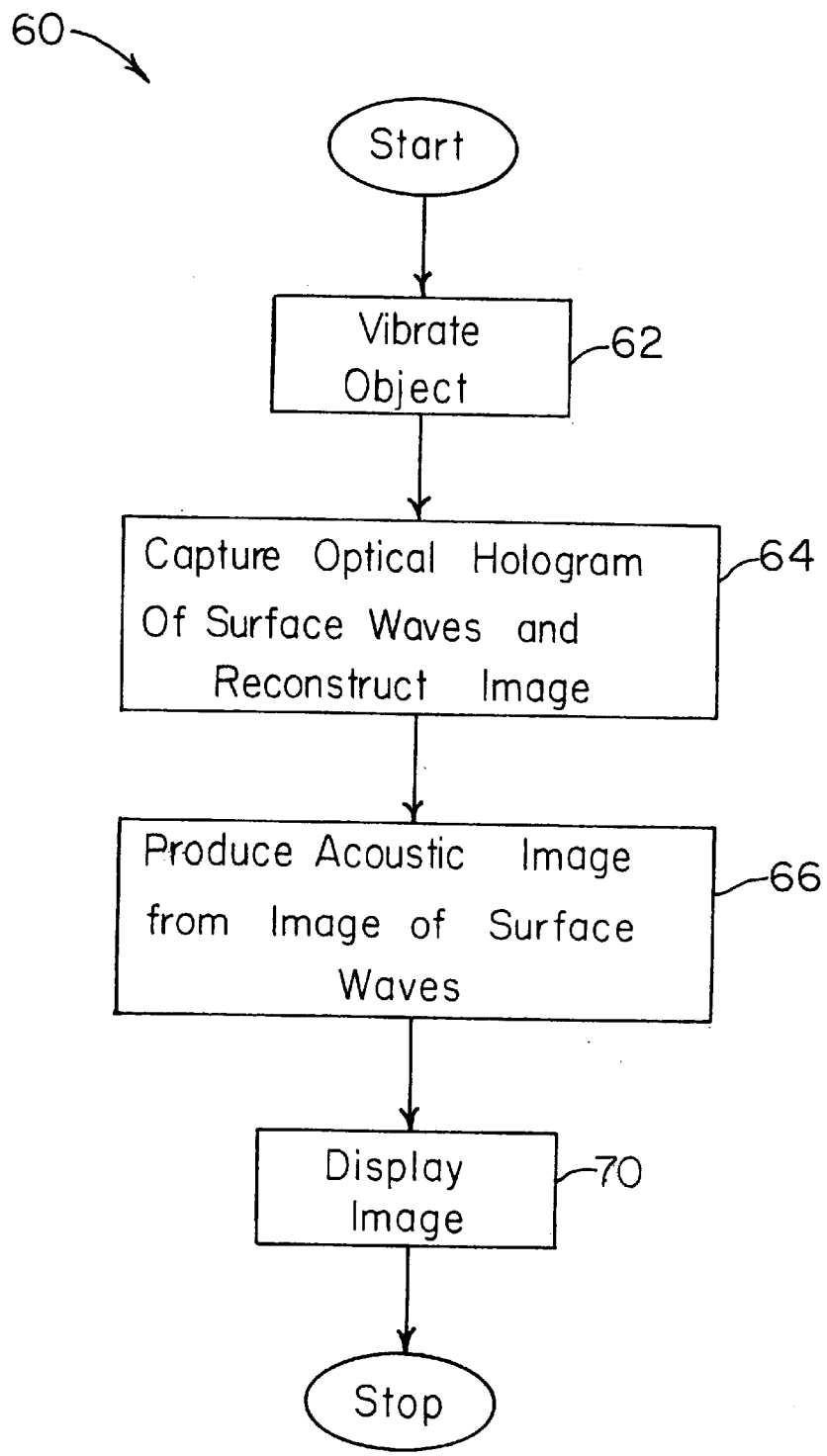
FIG. 5 is a flow chart representation of a method for producing an acoustic image according to one embodiment of the invention.

Referring now to FIG. 5, the acoustic imaging apparatus 10 may be operated according to a method 60 to produce the acoustic image of the object 12. Assuming that the photorefractive imaging system 14 is prepared and ready to produce an optical hologram of the surface 26 of object 12, the first step 62 in the method 60 is to vibrate the object 12 to produce one or more acoustic waves 20 therein. In the embodiment shown and described herein, the acoustic waves 20 are generated by excitation source 16. As will be described in greater detail below, it is generally preferred, but not required, that the excitation source 16 be operated in a "tone burst" mode to generate a finite number of coherent acoustic waves 20. Alternatively, the excitation source 16 could be operated in a continuous manner if sufficient acoustic wave absorbing materials (e.g., 74) are positioned adjacent the object 12.

In any event, the acoustic waves 20 produced by the excitation source 16 travel throughout the interior region of the object 12 (generally as elastic or compressive waves 22), and are reflected, diffracted, and otherwise disturbed by certain interior features, structures, and/or faults which may be contained within the object 12. For example, with reference now specifically to FIGS. 2b and 4, some of the acoustic waves 20 may interfere with a structural feature, such as a flat-bottomed hole 72, that may be provided in the object 12. After interacting with the hole 72, some of the elastic or compressive waves 22 will be reflected by the surface 26 of the object 12. The reflection process typically results in the formation of one or more surface displacements 24 on the surface 26 of object 12. These surface displacements 24 contain information relating to the flat-bottomed hole 72 contained within the object 12. Such information is generally embodied in certain phase and amplitude variations in the surface displacements 24.

In step 64 of the method 60, the photorefractive imaging system 14 produces an optical hologram (not shown) of the surface displacements 24 contained on the surface 26 of the object 12. The optical hologram (not shown) may then be used to reconstruct an image 50 (FIG. 4) that contains both the phase and amplitude variations contained in the surface displacements 24. As was briefly mentioned above, in certain applications it is possible that the reconstructed image 50 will contain sufficient "acoustic" image data to allow a user to ascertain the nature of the desired internal features, structures, and/or faults which may be contained in the object 12. If so, no additional processing steps may be required.

However, in most applications it will be necessary, or at least desirable, to further if process the data contained in the image 50 in order to produce an "acoustic" image that more readily illustrates the nature of the desired internal features, structures, and/or faults which may be contained in the object 12. If so, the method 60, may proceed to step 66 in which the image processing system 56 utilizes the data (e.g., phase and amplitude data) contained in the image 50 of the surface displacements 24 to produce an acoustic image of the object 12. As will be described in greater detail below, any of a wide range of acoustic imaging processes that are now known in the art or that may be developed in the future may be used to produce the acoustic image data. Thereafter, the acoustic image data (not shown) may be displayed on display device 58 in step 70 as an acoustic image (not shown). The acoustic image reveals certain interior features, structures, and/or faults contained within the object 12.

A significant advantage associated with the method and apparatus according to the present invention is that it collects the phase and amplitude information directly from the surface of the ensonified object. Consequently, the present invention is free of the distorting effects typically associated with prior art devices in which the acoustic wave must first travel through an intermediate medium (e.g., air or a liquid) before reaching the detection device. The present invention also dispenses with the need for microphones to sense the acoustic data, with all their associated disadvantages, such as limited spatial and/or temporal resolution. The present invention also does not require that the object be immersed in any liquid medium, which allows a wider range of objects to be examined and, of course, does away with the distortions associated with the passage of the acoustic waves through the liquid. As a result of the foregoing advantages, the present invention may be used to produce a high resolution, low distortion acoustic image of interior features, structures, and/or faults which may be contained in the object.

Having briefly described one embodiment of the method and apparatus for detecting internal structures in bulk objects, as well as some of their more significant advantages, the various embodiments of the method and apparatus according to the present invention will now be described in detail. However, before proceeding with the detailed description of the various embodiments, it should be noted that while the present invention is shown and described herein as it could be used to detect internal structures in a relatively simple object, such as a homogeneous block of aluminum having substantially uniform density, the present invention is not limited to use with such simple objects and can be used to detect internal structural configurations of almost any object imaginable, including living organisms, such as persons or animals. Consequently, the present invention should not be regarded as limited to the particular objects and examples shown and described herein.

With the foregoing considerations in mind, one embodiment of an apparatus 10 according to the present invention is shown and described herein as it may be used to capture acoustic wave data and to produce an acoustic image (not shown) of an object 12 based on the captured acoustic wave data. The acoustic image (not shown) may be used to reveal certain interior features, structures, and/or faults which may be located within the object 12.

Referring now to FIGS. 1 and 2a, the acoustic imaging apparatus 10 according to one preferred embodiment of the present invention may comprise an excitation source 16, such as an acoustic transducer 18, for ensonifying the object 12, i.e., for producing one or more acoustic waves 20 in the object 12. In the embodiment shown and described herein, the acoustic transducer 18 may be placed in contact with the object 12 so as to more efficiently couple to the object 12 the acoustic energy produced by the transducer 18. Alternatively, other arrangements may be used to ensonify the object 12, as would be obvious to persons having ordinary skill in the art after having become familiar with the teachings of the present invention.

It is generally preferred, but not required, that the acoustic transducer 18 be operated in a "tone burst mode" in which the acoustic transducer 18 is operated to produce a finite number of acoustic waves during a finite time or "burst" period. Operating the acoustic transducer 18 in such a tone burst mode limits interference effects resulting from reflected elastic or compressive waves (e.g., waves 22') contained within the object 12. That is, it is generally preferred to capture data relating to the surface displacements 24 before such reflected elastic or compressive waves 22' have a chance to appear on the surface 26 of object 12. In this regard it is also generally preferred, but not required, to place an acoustic wave absorbing material 74 adjacent those surfaces of the object 12 that are not to be examined. Such an acoustic wave absorbing material 74 reduces the likelihood that elastic or compressive waves 22 and 22' will be reflected back to the surface 26 being studied and interfere with the surface displacements 24 contained thereon.

Any of a wide range of acoustic frequencies generated for any of a wide range of fixed time periods may be used to ensonify the object 12 in the manner just described. Consequently, the present invention should not be regarded as limited to any particular frequencies produced for any particular time or "burst" periods. However, by way of example, in one preferred embodiment, the acoustic transducer generates acoustic waves having a frequency of about 2500 kilohertz (kHz). The time or "burst" period for when such waves may be generated will generally depend on the size, shape, and composition of the object. That is, the burst period should be selected so that it is sufficiently short so that there will not be time for the acoustic waves to be reflected internally and then return to the surface being imaged, thereby distorting the surface displacements 24. The deleterious effects of such internal wave reflections can also be reduced by placing acoustic wave absorbing material 74 adjacent those surfaces of the object 12 that are not currently being examined. By way of example, in one preferred embodiment, the acoustic waves may be generated for burst periods of about 1 millisecond, although other times could also be used in accordance with the foregoing considerations.

In accordance with the foregoing operational requirements, the acoustic transducer 18 may comprise any of a wide range of devices well-known in the art for producing acoustic waves. Consequently, the present invention should not be regarded as limited to any particular type of transducer. However, by way of example, in one preferred embodiment of the present invention, the acoustic transducer 18 may comprise a piezo-electric transducer which may be operated by a suitable transducer power supply assembly 17. The transducer power supply assembly 17 may be controlled by a "master" function generator 13 which allows the transducer 18 to produce acoustic waves of the desired frequency and for the desired burst period.

As was described above, the acoustic waves 20 produced in the object 12 by the excitation source 16 (e.g., acoustic transducer 18) may comprise one or more elastic or compressive waves 22 which typically result in the formation of one or more surface displacements 24. The elastic or compressive waves 22 exist generally within the object 12, whereas the surface displacements 24 are formed on the surface 26 of object 12 by the reflection of the elastic or compressive waves 22 by the surface 26. That is, when an elastic or compressive wave 22 is incident on the surface 26, some of the energy contained in the incident elastic or compressive wave 22 will be reflected by the surface 26 as reflected elastic or compressive wave 22'. However, the reflection will also result in the formation of one or more surface displacements 24.

Figure 3:
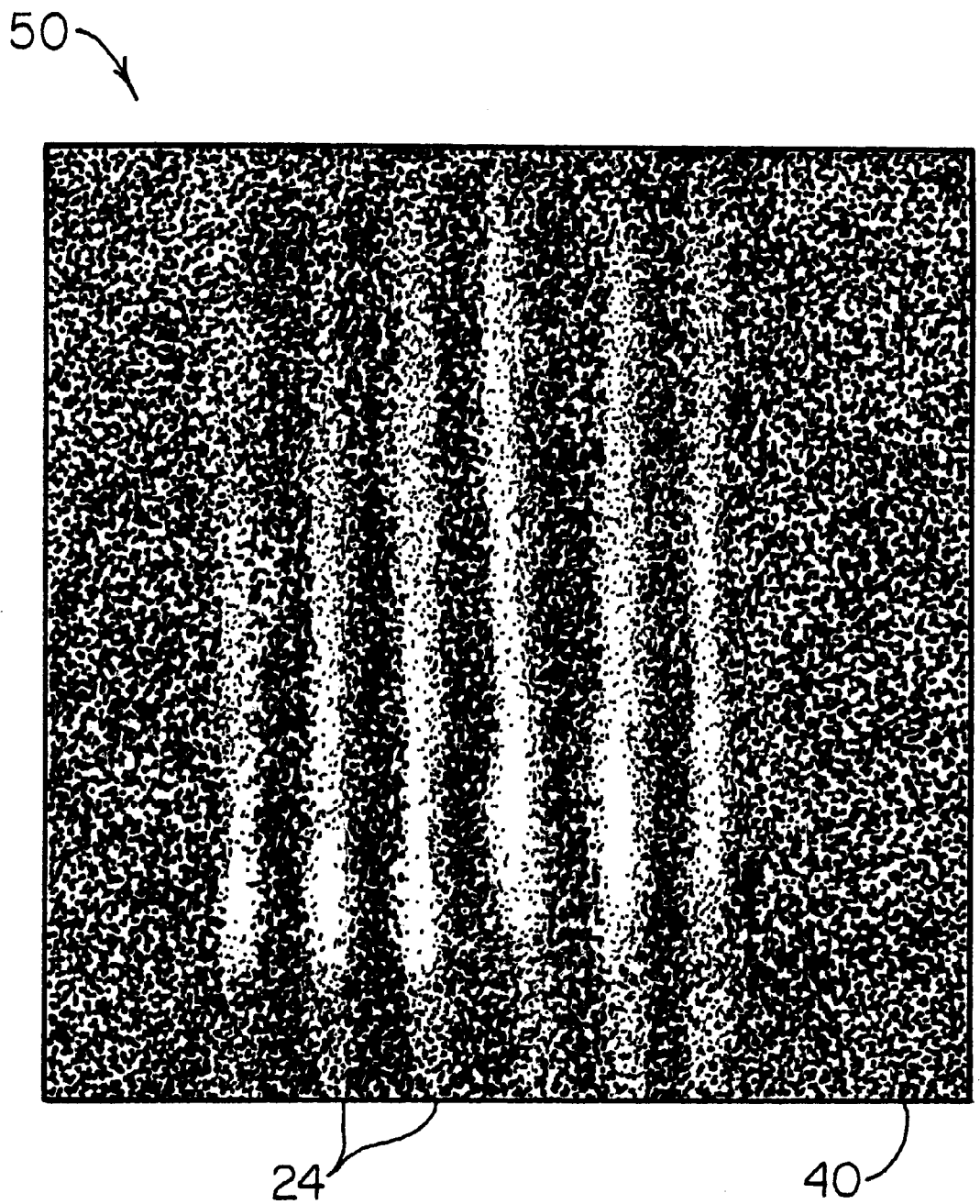
FIG. 3 is a diagrammatic representation of an image of surface displacements on a first portion of the object illustrated in FIG. 2(a) reconstructed from an optical hologram produced by the photorefractive imaging system.

The form of the surface displacements 24 is influenced by numerous factors, including, without limitation, the shape of the object, its density, as well as certain features, structures, and or faults that may be contained either on the surface or within the interior of the object 12. This phenomenon may be better understood by considering a few examples. Consider, as a first example, the situation illustrated in FIG. 2a wherein the object 12 comprises a generally homogeneous aluminum block of substantially uniform density. Acoustic waves 22 produced by the transducer 18 are not substantially altered as they pass through the object 12. The result is the formation of a generally uniform distribution of surface displacements 24 on the surface of the object 12, as best seen in FIG. 3. However, in a second example, illustrated in FIG. 2b, a second portion of the object 12 (i.e., the homogeneous aluminum block of substantially uniform density) is provided with a flat-bottomed hole 72 therein. When this portion of the object 12 is ensonified by acoustic waves 20 produced by the excitation source 16 positioned substantially as shown in FIG. 2b, the presence of the flat-bottomed hole 72 in the object 12 results in the formation of a surface displacement pattern having phase and amplitude variations substantially as shown in FIG. 4. It is these phase and amplitude variations that are captured by the present invention which may be used to produce an acoustic image of the object 12.

Referring back now to FIG. 1, the phase and amplitude variations of the surface displacements 24 on the surface 26 of the object 12 are detected with the aid of the photorefractive imaging system 14. In the embodiment shown and described herein, the photorefractive imaging system 14 may comprise a photorefractive imaging system of the type shown and described in U.S. patent application Ser. No. 09/112,075, filed on Jul. 8, 1998, and entitled "Apparatus and Method for Measuring and Imaging Traveling Waves" of Telschow and Deason, which is incorporated herein by reference for all that it discloses.

Briefly, the photorefractive imaging system 14 disclosed in the above-referenced patent application may comprise a light source assembly 28 which produces two mutually coherent optical (e.g., light) beams or wavefronts: An optical object beam or wavefront 30 and an optical reference beam or wavefront 32. The optical object and reference beams 30 and 32 are preferably derived from a single, coherent source beam 76 produced by the light source assembly 28.

The light source assembly 28 which may be used to generate the single, coherent optical source beam 76 may comprise any of a wide range of lasers that are now known in the art or that may be developed in the future that would be suitable for producing such a coherent optical source beam 76. By way of example, in one preferred embodiment of the present invention, the light source 28 may comprise a 200 milliwatt (mw) argon laser capable of producing a coherent optical source beam having a wavelength of about 514 nanometers (nm). Alternatively, lasers having other output powers and beam wavelengths could also be used.

The optical source beam 76 produced by the light source assembly 28 (e.g., laser) first may be directed through a half wave plate 78 before being directed to a beam splitter 80 which splits the optical source beam 76 into the optical object beam 30 and the optical reference beam 32. Thereafter, the optical object beam 30 may be directed to a beam confining and directing device 34 which directs the optical object beam 30 onto the surface 26 of object 12 as an expanded optical object beam 38. While any of a wide range of components or combinations of components may be used to direct the optical object beam 30 onto the object 12, in one preferred embodiment, the beam directing device 34 may comprise a beam coupling lens 82 and optic fiber or light pipe assembly 36. Such an arrangement converts the optical object beam 30 into an expanded, generally cone-shaped optical beam 38 and allows the expanded optical beam 38 to be conveniently directed onto the desired portion of the surface 26 of object 12 to illuminate a two-dimensional area or region 40 (e.g., FIGS. 3, 4) thereof.

The various components described above (e.g., beam splitter 80, coupling lens assembly 82, and optic fiber assembly 36) for producing the expanded optical object beam 38 and for directing it onto the surface 26 of object 12 may comprise any of a wide range components and devices that are well-known m the art and readily commercially available. Consequently, the particular beam splitter 80, coupling lens assembly 82, and optic fiber assembly 36 which may be utilized in one preferred embodiment of the present invention will not be described in further detail herein.

The surface displacements 24 on the surface 26 of object 12 modulate the phase of the expanded optical object beam 38 to produce modulated optical object beam 42. Thereafter, phase modulated optical object beam 42 is collected by a collection lens 84 which focuses the modulated optical object beam 42 onto the photorefractive sensing medium 48. A polarizer 86 positioned between the collection lens 84 and the photorefractive sensing medium 48 may comprise a high extinction ratio polarizer to select one polarization component of the modulated optical object beam 42 for passage onto the photorefractive sensing medium 48.

The optical reference beam 32 emerging from the beam splitter 80 is directed through a beam modulator 44 which modulates the phase of the optical reference beam 32 to produce a modulated optical reference beam 46. In the embodiment shown and described herein, the bean modulator 44 comprises an electro-optic modulator of the type well-known in the art for modulating the phase of the optical reference beam 32. A synchronizer 88 synchronizes signals (not shown) produced by master and slave function generators 13 and 15 in a manner that will be described below and operates the beam modulator 44 so that beam modulator 44 modulates the phase of the optical reference beam 32 at a frequency that is slightly different than the frequency of the phase modulation of the modulated optical object beam 42. For example, and as will be described in greater detail below, the synchronizer 88 operates the beam modulator 44 so that it modulates the phase of the optical reference beam at a frequency of about 25 Hz. Alternatively, other frequencies may also be used as would be obvious to persons having ordinary skill in the art after having become familiar with the teachings of the present invention.

After being modulated by beam modulator 44, the modulated optical reference beam 46 may be expanded by a suitable beam expander assembly 90 which, in one preferred embodiment may comprise a pair of lenses 92 and 94. A polarizer 96 positioned between the beam expander assembly 90 and the photorefractive sensing medium 48 selects (i.e., discriminates) a polarization component of the modulated optical reference beam 46 for passage to the photorefractive sensing medium 48. Polarizer 96 may comprise a high extinction ratio polarizer of the type well known in the art and readily commercially available.

The sensing medium 48 may comprise a photorefractive substance, such as a bismuth silicon oxide crystal. When the modulated optical object and reference beams 42 and 46 are re-combined within the sensing medium 48, they create a space charge field (not shown) having a magnitude that is directly proportional to the vibrational displacement or amplitude of the surface displacements 24 on the surface 26 of object 12. The magnitude of the space charge field is also related to a cosine function of the vibration phase of the surface displacements 24, at least for small amplitude displacements. The space charge field modulates the local refractive index of the sensing medium 48 by the electro-optical effect, creating a diffraction grating within the sensing medium 48 that embodies the desired low-frequency phase information. The result is the formation of a hologram (not shown) from which may be reconstructed an image 50 (illustrated generally in FIGS. 3 and 4) of the surface displacements 24 on the surface 26 of object 12. The intensity variations of the reconstructed image 50 are proportional to the phase difference between the modulated object and reference beams 42 and 46, respectively, thus the surface displacements 24.

Since the modulated optical reference beam 46 has been modulated at a rate that is very close to but different than the frequency of the surface displacements 24, the features of the reconstructed image 50 will move at a speed that is related to the frequency difference between the modulated optical object beam 42 and the modulated optical reference beam 46. Since, as was mentioned above, the photorefractive material comprising the sensing medium 48 has an intrinsic response time (i.e., cut-off frequency), the offset or difference frequency between the modulated optical object and reference beams 42 and 46 must be below the cut-off frequency of the photorefractive material 48. If the difference frequency is too great, the resulting hologram will move so rapidly that the photorefractive material 48 will fail to record the change. This provides a significant advantage of the present invention. That is, the bandpass filtering provided by the sensing medium 48 filters or removes disturbances having frequencies such that the difference frequencies between the disturbances and the modulated optical reference beam 42 are greater than the frequency response of the sensing medium 48.

The bismuth silicon oxide material which may comprise the photorefractive sensing medium 48 in one preferred embodiment has a high frequency cut-off of about 67Hz. Alternatively, photorefractive sensing media having other high frequency cut-offs (e.g., high frequency cut-offs of about 1 kHz) are known and may be used as well. In any event, in order to detect surface displacements 24, the optical reference beam 32 should be modulated at a frequency so that the difference frequency between the modulated optical reference beam 46 and the modulated optical object beam 42 does not exceed the high frequency cut-off of the photorefractive sensing medium 48. In accordance with the foregoing considerations; then, the synchronizer 88 in one preferred embodiment of the present invention operates in the manner described below to modulate the phase of the optical reference beam 32 at a frequency that is about ±25 Hz from the frequency of the modulated optical object beam 42. For example, if it is desired to examine surface displacements having frequencies of about 40 kHz, then it will be desirable to modulate the phase of the optical reference beam 32 at a frequency of about 40 kHz±25 Hz. Similarly, if surface displacements 24 having frequencies of about 100 kHz are to be examined, then the optical reference beam 32 should be modulated at a frequency of about 100 kHz±25 Hz.

The reconstructed image 50 produced in the photorefractive sensing medium 48 may be observed by means of a suitable array (i.e., two-dimensional) detector 52, such as a CCD-type video camera 54. Alternatively, the reconstructed image 50 may by directly observed by the human eye via an eyepiece (not shown) or other such device. Finally, depending on the type of detector 52 utilized, it may be necessary to position a focusing lens 99 between the detector 52 and the photorefractive sensing medium 48.

If a video camera 54 is used to detect the reconstructed image 50, the video camera 54 maybe connected to an image processing system 56. Image processing system 56 may be used to process the electronic image data signals (not shown) produced by the camera 54 and to construct an acoustic image of the object 12 based on the phase and amplitude of the surface displacements 24 on the surface 26 of object 12. As mentioned above, the acoustic image may reveal certain interior features, structures, and/or faults that may be contained within the object 12. The acoustic image may be displayed on the display device 58.

As was briefly discussed above, it is generally preferred, but not required, to utilize an image data processing system 56 in order to further process the data contained in the image 50 produced by the photorefractive imaging system 14. However, it is possible that in certain applications, sufficient information about the object 12 may be gleaned from the image 50 without further processing. For example, if a particular internal structural feature is to be looked for, it is possible that a trained observer looking at the real time image 50 will be capable of ascertaining whether the desired feature is present or not. If this is the case, it is not necessary to perform any additional processing of the data contained in the image 50, since the presence or absence of the desired structural feature can be determined directly from an examination of the image 50.

However, in most applications it will be necessary, or at least desirable, to further process the data contained in the image 50 in order to produce an acoustic image which may more readily show or illustrate the desired internal features, structures, and/or faults which may be contained within the object 12. If so, it will be desirable to provide the invention with the image data processing system 56. The image data processing system 56 utilized in one preferred embodiment of the present invention may comprise a general purpose programmable computer, such as a personal computer, of the type that are well-known in the art and that are readily commercially available. The image data processing system 56 may be programmed to produce an acoustic image based on the data contained in the image 50 produced by the photorefractive imaging system 14.

The acoustic image may be produced according to the method 60 illustrated in FIG. 5. Assuming that the photorefractive imaging system 14 is prepared and ready to produce an optical hologram (not shown) of the surface 26 of the object 12, the first step 62 in the method 60 is to vibrate the object 12 to produce one or more acoustic waves 20 therein. In one preferred embodiment, the acoustic waves 20 are produced by the acoustic transducer 18. As described above, it is generally preferred, but not required, to operate the acoustic transducer 18 in a tone burst mode to generate a finite number of acoustic waves 20 during a finite time or "burst" period. Operation of the acoustic transducer 18 in such a tone burst mode may be accomplished by means of the master function generator 13 and the transducer power supply 17. However, since such function generators and transducer power supplies are well-known in the art and since methods for operating such devices to produce a tone burst are also well-known in the art and could be easily provided by persons having ordinary skill in the art after having become familiar with the teachings of the present invention, the particular methods for operating the foregoing devices to produce a tone burst will not be described in further detail herein.

The acoustic waves 20 produced by the acoustic transducer 18 travel throughout the interior region of the object 12, typically in the form of elastic or compressive waves 22, and are reflected, diffracted, phase-shifted, and otherwise disturbed by certain interior features of the object 12. After interacting with such features, some of the elastic or compressive waves 22 will be incident on the surface 26 of object 12, resulting in the formation of one or more surface displacements 24. These surface displacements 24 contain information relating to certain features (e.g., hole 72, FIG. 2b) in the object 12. Such information is generally embodied in certain phase and amplitude variations in the surface displacements 24, as best seen in FIG. 4.

In step 64 of method 60, the photorefractive imaging system 14 produces an optical hologram of the surface displacements 24 contained on the surface 26 of the object 12. The optical hologram is then used to reconstruct an image (e.g., image 50 illustrated in either FIGS. 3. or 4) that contains both the phase and amplitude variations embodied in the surface displacements 24. As discussed above, in certain applications it is possible that the reconstructed image 50 will contain sufficient "acoustic" image data to allow a user to ascertain the nature of the desired internal features, structures, and/or faults which may be contained in the object 12. If so, no additional processing steps may be required.

However, in most applications it will be necessary, or at least desirable, to further process the data contained in the image 50 in order to produce an "acoustic" image that more readily illustrates the nature of the desired internal features, structures, and/or faults which may be contained in the object 12. If so, the method 60 may proceed to step 66 in which the image processing system 56 utilizes the data (e.g., phase and amplitude data) contained in the image 50 of the surface displacements 24 to produce an acoustic image of the object 12.

Any of a wide range of methods now known in the art or that may be developed in the future may be used by the image processing system 56 to produce an acoustic image from the image 50 formed by the photorefractive imaging system 14. For example, the acoustic image may be produced according to a discrete convolution process of the type it described in a paper entitled "Holographic Reconstruction of Acoustic Fields by Discrete Convolution" published in *Acoustical Imaging*, Vol. 23, pp. 453–458, Plenum Press, 1997, which is incorporated herein by reference for all that it discloses. Alternatively, the acoustic image could be constructed by an angular spectrum method, such as that described in a paper entitled "Field Propagation via the Angular Spectrum Method" published in *Acoustical Imaging*, Vol. 23, pp. 363–369, Plenum Press, 1997, which is also incorporated herein by reference for all that it discloses. In still another alternative, the acoustic image may be constructed by a method of diffracted waves and canonical solutions, such as the method described in a paper entitled "Shape Reconstruction of a Penetrable Scattering Body via Diffracted Waves and Canonical Solutions" published in *Acoustical Imaging*, Vol. 23, pp. 459–464, Plenum Press, 1997, which is incorporated herein by reference for all that it discloses. In still another application, the data contained in the image 50 may be processed in accordance with tomography-type data processing methods in order to produce acoustic tomograms of the object 12. However, since methods for producing acoustic images based on phase and amplitude information of surface displacements, such as those referred to above, are well-known in the art and could be easily provided by persons having ordinary skill in the art after having become familiar with the teachings of the present invention, the particular method and program that may be utilized in one preferred embodiment will not be described in greater detail therein. Once the acoustic image is produced, the image processing system 56 may display the acoustic image on display device 58 at step 70.

This completes the detailed description of the various embodiments of the method and apparatus according to the present invention. While a number of specific components were described above for the preferred embodiments of this invention, persons having ordinary skill in the art will readily recognize that other substitute components or combinations of components may be available now or in the future to accomplish comparable functions to the various components shown and described herein. Accordingly, it should be understood that the inventive concepts herein described may be variously otherwise embodied and it is intended that the appended claims be construed to include alternative embodiments of the invention except insofar as limited by the prior art.

We claim:

1. A method for detecting an internal structure in an object, comprising:

vibrating the object to produce at least one acoustic wave therein, the acoustic wave resulting in at least one surface displacement on a surface of the object;

directing an object wavefront toward the surface of the object so that said object wavefront is modulated by the surface displacement on the object to produce a modulated object wavefront;

modulating a reference wavefront in synchronization with the vibrating object to produce a modulated reference wavefront so that a difference frequency between the modulated object wavefront and the modulated reference wavefront is within the response range of a sensing medium;

combining the modulated object wavefront and the modulated reference wavefront within the sensing medium to produce an image relating to the surface displacement on the object; and detecting an internal feature of the object based on the image relating to the surface displacement.

2. The method of claim 1, wherein the step of vibrating the object comprises the step of vibrating the object at an ultrasonic frequency.

3. The method of claim 1, wherein the step of vibrating the object comprises the step of vibrating the object with a tone-burst pulse.

4. The method of claim 1, wherein the step of determining information about an internal feature of the object based on the surface displacement includes the step of producing an acoustic image based on the phase and amplitude of the surface displacement.

5. The method of claim 4, wherein the acoustic image is produced by a discrete convolution process.

6. The method of claim 4, wherein the acoustic image is produced by an angular spectrum method.

7. The method of claim 4, wherein the acoustic image is produced by a method of diffracted waves and canonical solutions.

8. Apparatus for producing an acoustic image of an internal structure of an object, comprising:

an excitation source operatively associated with the object, the excitation source vibrating the object to produce at least one acoustic wave therein, the acoustic wave resulting in at least one surface displacement on a surface of the object;

a light source positioned a spaced distance from the object, said light source producing an optical object wavefront and an optical reference wavefront, said light source directing the optical object wavefront toward the surface of the object to produce a modulated optical object wavefront;

a modulator operatively associated with the optical reference wavefront, said modulator modulating the optical reference wavefront in synchronization with the acoustic wave to produce a modulated optical reference wavefront;

a sensing medium positioned to receive the modulated optical object wavefront and the modulated optical reference wavefront, the sensing medium having a response range, the modulated optical reference wavefront being modulated by said modulator so that a difference frequency between the modulated optical object wavefront and the modulated optical reference wavefront is within the response range of said sensing medium, the modulated optical object wavefront and the modulated optical reference wavefront combining in said sensing medium to produce an image related to surface displacement on the surface of the object;

a detector operatively associated with said sensing medium, said detector detecting the image related to the surface displacement; and an an image processing system operatively associated with said detector, said processing system producing the acoustic image of the internal structure based on the surface displacement.

9. The apparatus of claim 8, wherein said light source comprises a laser.

10. The apparatus of claim 9, wherein said sensing medium comprises a photorefractive material, the modulated optical object wavefront and the modulated optical reference wavefront interfering with one another within said photorefractive material to generate a space charge field within the photorefractive material.

11. The apparatus of claim 8, wherein said optical object wavefront comprises an object beam of coherent light and wherein said optical reference wavefront comprises a reference beam of coherent light.

12. The apparatus of claim 8, wherein said modulator comprises a phase modulator for modulating a phase of said optical reference wavefront.

13. The apparatus of claim 8, wherein said detector comprises a video camera.

14. The apparatus of claim 8, wherein said light source comprises a beam splitter for producing the optical object wavefront and the optical reference wavefront from a single wavefront.

15. Apparatus for producing an acoustic image of an internal structure of an object, comprising:

acoustic transducer means for producing at least one acoustic wave in the object, the at least one acoustic wave resulting in at least one surface displacement on the surface of the object, the surface displacement having a phase and an amplitude;

photorefractive imaging means positioned a spaced distance from the object for producing an image related to the surface displacement on the object, the image including information relating to the phase and the amplitude of the surface displacement;

image data processing means operatively associated with said photorefractive imaging means for constructing the acoustic image of the internal structure based on the information relating to the phase and amplitude of the surface displacement.

16. A method for detecting an internal structure of an object, comprising:

providing a sensing medium, said sensing medium having a response range;

producing an object wavefront and a reference wavefront;

vibrating the object to produce a surface displacement on a surface of the object, the surface displacement having a phase and an amplitude;

directing the object wavefront toward the surface of the object so that said object wavefront is modulated by the surface displacement to produce a modulated object wavefront;

modulating the reference wavefront in synchronization with the vibrating object to produce a modulated reference wavefront so that a difference frequency between the modulated object wavefront and the modulated reference wavefront is within the response range of the sensing medium;

combining the modulated object wavefront and the modulated reference wavefront within the sensing medium to produce an image related to the surface displacement on the surface of the object, the image including information relating to the phase and the amplitude of the surface displacement;

detecting the image related to the surface displacement; and detecting the internal structure of the object based on the phase and amplitude of the surface displacement.

* * * * *